(12) United States Patent
Chang et al.

(10) Patent No.: US 7,906,155 B2
(45) Date of Patent: Mar. 15, 2011

(54) METHOD FOR INCREASING AN AMOUNT OF EFFECTIVE CONSTITUENTS FROM A PLANT IN A SOLVENT

(75) Inventors: Kai-Hsuan Chang, Taipei (TW); Ming-Yu Lin, Taipei (TW); Yung-Sheng Lin, Taipei (TW); Ting-Kai Leung, Taipei (TW)

(73) Assignees: National Applied Research Laboratories, Taipei (TW); Taipei Medical University, Taipei (TW)

( * ) Notice: Subject to any disclaimer, the term of this patent is extended or adjusted under 35 U.S.C. 154(b) by 643 days.

(21) Appl. No.: 11/856,981

(22) Filed: Sep. 18, 2007

(65) Prior Publication Data

US 2008/0308408 A1    Dec. 18, 2008

(30) Foreign Application Priority Data

Jun. 13, 2007    (TW) ............................... 96121436 A

(51) Int. Cl.
*A61K 36/00*    (2006.01)

(52) U.S. Cl. ...................................................... 424/725

(58) Field of Classification Search ........................ None
See application file for complete search history.

(56) References Cited

U.S. PATENT DOCUMENTS

| 4,927,651 A | * | 5/1990 | Kumani et al. | 426/324 |
| 6,497,908 B1 | * | 12/2002 | Oshiro | 426/238 |
| 7,595,066 B2 | * | 9/2009 | Kim | 424/725 |
| 2002/0139963 A1 | * | 10/2002 | Kim | 252/582 |

FOREIGN PATENT DOCUMENTS

| JP | 03075256 A | | 3/1991 |
| JP | 03175916 A | | 7/1991 |
| JP | 07135955 | * | 5/1995 |
| JP | 07135955 A | | 5/1995 |
| JP | 07136670 A | | 5/1995 |
| JP | 07148231 | * | 6/1995 |
| JP | 08098897 A | | 4/1996 |
| JP | 10241728 | * | 9/1998 |
| JP | 2004018850 A | | 1/2004 |
| JP | 2004180664 | * | 7/2004 |
| KR | 2003080629 | * | 10/2003 |
| KR | 1020040101728 A | | 12/2004 |
| KR | 2006108281 | * | 10/2006 |

* cited by examiner

*Primary Examiner* — Christopher R. Tate
(74) *Attorney, Agent, or Firm* — Volpe and Koenig P.C.

(57) ABSTRACT

A method for increasing an amount of effective constituents from a plant in a solvent is provided. The method comprises steps of treating the solvent with a far-infrared radiating (FIR) material and extracting the effective constituents from the plant by the treated solvent for increasing the amount of the effective constituents dissolved in the solvent.

10 Claims, 2 Drawing Sheets

METHOD FOR INCREASING AN AMOUNT OF EFFECTIVE CONSTITUENTS FROM A PLANT IN A SOLVENT

FIELD OF THE INVENTION

The present invention is related to a method for increasing an amount of effective constituents from a plant in a solvent. More particularly, the present invention is related to a method for increasing an amount of effective constituents from a plant in a solvent via a far infrared (FIR) ray radiated by an FIR material.

BACKGROUND OF THE INVENTION

So far, many effective constituents of Chinese herbs or perfumes are secondary metabolites of plants. Secondary metabolites are organic compounds that are not directly involved in the normal growth, development or reproduction of organisms. These organic compounds, which have wide varieties and the chemical structures thereof are respectively different, could be classified to three types, phenolic compounds, isoprepenoid compounds, and nitro-organic compounds. The application of the secondary metabolites of plants is very wide, wherein they can be used in industries of medicine, chemical, food and agriculture and so on.

Taking the Chinese herbs for example, the obtainment of many Chinese herbs is not easy, because many wild Chinese herbs are threatened as a result of over-harvesting and habitat loss, or some Chinese herbs is not easy to culture due to the limitation of the growth condition. Therefore, the secondary metabolites of the Chinese herbs are valuable and scarce. Furthermore, the content of some target secondary metabolites in the nature plants is too low, for example, the content of the taxol in the bark of the pacific yew tree is only 0.02%, which causes the supply of the secondary metabolites to be far from satisfying the market requirements. Accordingly, how to effectively obtain the most amount target secondary metabolites from plants becomes an important subject.

People try to use chemical synthesis method to solve the problem about the limiting resource, but the method is not suitable for all kinds of the effective constituents from plants and the method has the problems of complicated process, high cost, stereoisomer forming during the process of the synthesis, and environmental contamination and so on.

Therefore, because of the defects in the prior arts, the inventors provide a method for increasing an amount of effective constituents from a plant in a solvent to effectively overcome the demerits existing in the prior arts.

SUMMARY OF THE INVENTION

The present invention provides a method for increasing an amount of effective constituents from a plant in a solvent for overcoming the defects of the high cost and the complicated processes existing in the prior arts due to producing plant effective constituents by the chemical synthesis method.

In accordance with an aspect of the present invention, a method for increasing an amount of effective constituents from a plant in a solvent is provided. The method comprises steps of treating the solvent with a far-infrared (FIR) radiating material; and extracting the effective constituents from the plant by the treated solvent for increasing the amount of the effective constituents dissolved in the solvent.

Preferably, the method further comprises a step of cooling before the step of extracting the effective constituents from the plant by the treated solvent.

Preferably, the method further comprises a step of heating before the step of extracting the effective constituents from the plant by the treated solvent.

Preferably, the step of treating the solvent with the FIR radiating material is processed under room temperature.

Preferably, a major composition of the FIR material is an oxidized mineral.

Preferably, the oxidized mineral comprises 60-95% by weight of an aluminum oxide.

Preferably, the FIR radiating material comprises 1-20% by weight of an iron oxide.

Preferably, the FIR radiating material comprises 1-20% by weight of a magnesium oxide.

Preferably, the FIR radiating material comprises 1-30% by weight of a calcium carbonate.

Preferably, the solvent is a liquid.

Preferably, the solvent is one of water and an organic solvent.

Preferably, the plant is a Chinese herb and the effective constituents are chemical constituents.

In accordance with another aspect of the present invention, an auxiliary composition for increasing an amount of effective constituents from a plant in a solvent is provided. The auxiliary composition comprises a far-infrared (FIR) radiating material, wherein a major composition of the FIR material is an oxidized mineral, and the composition increases the amount of effective constituents from the plant in the solvent by a radiation of the FIR radiating material.

Preferably, the FIR radiating material radiates an FIR ray under room temperature.

Preferably, the oxidized mineral comprises 60-95% by weight of an aluminum oxide.

Preferably, the oxidized mineral comprises 1-20% by weight of an iron oxide.

Preferably, the oxidized mineral comprises 1-20% by weight of a magnesium oxide.

Preferably, the oxidized mineral comprises 1-30% by weight of a calcium carbonate.

Preferably, the solvent is one of water and an organic solution.

Preferably, the plant is a Chinese herb.

The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

Figure 1:
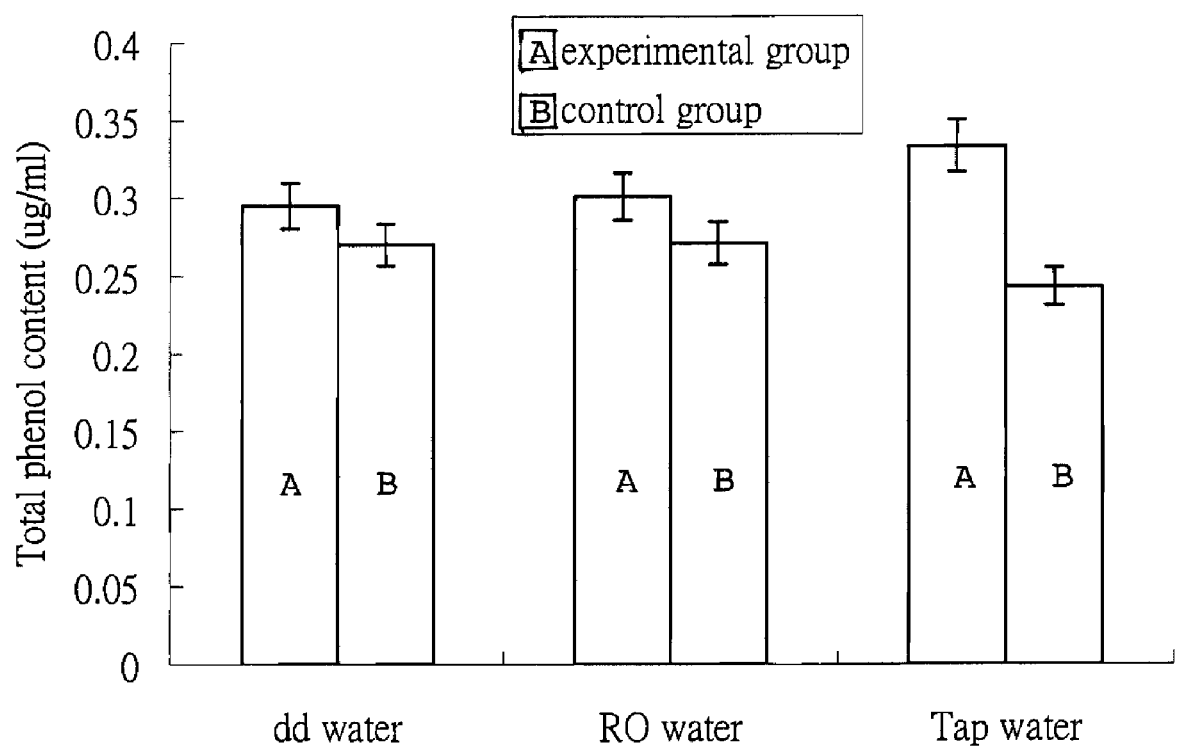
FIG. 1 is a diagram showing the effect of the FIR materials of the present invention on the total phenol contents of tea.

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

The First Embodiment

The FIR materials, which are developed by National Applied Research Laboratories and Taipei Medical University, used in this embodiment had been proved by many experiments for its biological effects. The composition of the FIR materials used in the present invention is composed of the major composition of several natural minerals, which includes 60-95% by weight of an aluminum oxide, 1-20% by weight of an iron oxide, 1-10% by weight of a magnesium oxide and 1-10% by weight of a calcium carbonate. Other compositions of the FIR materials could further include a titanium dioxide, a titanium boride or even more compositions of the nature minerals, such as a silicon oxide, a zinc hydroxide, a zinc oxide and a carbide and so on. The FIR materials show an FIR emissivity, which is detected by an FIR spectrometer, of higher than 0.98 compared to the black body within the wavelength of 6 to 14 micron range. Besides, the FIR ray emitted by the FIR materials has excellent antibacterial effects of over 99.9% both on *Staphylococcus aureus* (SA) and *Escherichia coli* (E-coli), which is evidenced by the recognized test protocol AATCC 100.

The foregoing FIR materials are used to treat extraction water for 20 hours and the FIR materials are not required to directly contact the extraction water during the treatment. Longer treating time has a better effect on the extraction; however, the treatment time of 20 hours is long enough to see an apparent difference. Herbal ingredients are soaked in the treated water and boiled for a predetermined time, which is depending on the properties of the herbal ingredients. The remaining liquid should then be filtered and the dregs of the herbal ingredients are removed, and the remaining decoction containing various effective contents of the herbal ingredients is the crude extract thereof. Pre-treating the extraction water with FIR materials increases an amount of the effective constituents dissolved in the decoction, thereby achieving a most effective release of the effective constituents from the fixed amount of the Chinese herbs.

The present invention is particularly suitable for valued Chinese herbs, such as a tortoise shell and a Dendrobium. Sometimes the same set of ingredients is boiled more than two or three times for extracting more effective constituents, most of which are chemical constituents, from the valued herbal ingredients. The extraction water pretreated with FIR materials has the functions of increasing the solubility of the effective constituents and shortening the length and the number of the decoction time. Therefore, besides the valued Chinese herbs, the present invention is also particularly suitable for Chinese herbs that need long decocting time, such as a hawksbill carapace and a nacre, wherein the effective constituents thereof are usually distributed among the intervals between tissues and are difficult to extract accordingly. Using the method provided in the present invention will obtain the same amount of the effective constituents in a relatively shorter time.

The mentioned herb decoction could be made into concentrated powders by a concentration process and a drying process or further made into pills, capsules, tablets, or film coated tablets, which are portable and convenient to swallow by adding different excipients and additives. Moreover, the foregoing method for making herb decoction could also be used to manufacture a biological pesticide for preventing plant diseases.

The Second Embodiment

The properties, such as the composition and the effects, of the FIR materials used in this embodiment are identical to the ones used in the first embodiment, and thus they will not be described again.

Some kinds of effective constituents from plants need to be extracted by organic solvents for a better extraction effect. The present invention could also be used in the process of obtaining those effective constituents from plants by an organic solvent.

In this embodiment, an organic solvent is treated with the foregoing FIR materials for 20 hours. The ground herbal ingredients are extracted by the treated organic solvent for obtaining a crude extract of the herbal ingredients. Depending on circumstances, a further purification or a separation processes might be performed after the extraction for obtaining the target effective constituent in the crude extract, and if the target effective constituent is a heat sensitive chemical constituent, then a cooling step is necessary for the extraction and the following processes. The extraction methods by organic solvents include a circumfluence extraction method and a continuous circumfluence extraction method, and both of the methods are suitable for the present invention which shorten the extraction time and reduce the use of organic solvents.

The Third Embodiment

The properties, such as the composition and the effects, of the FIR materials used in this embodiment are identical to the ones used in the first embodiment, and thus they will not be described again.

Three kinds of water samples, distilled de-ionized (dd) water, reverse osmosis (RO) water and tap water, are used in this embodiment and they are put into the centrifuge tubes respectively and the centrifuge tubes are put into the FIR materials for 20 hours. Dry tealeaves with the same weight are put into the respective three pretreated water samples for 10 minutes for serving as the experimental groups and three untreated water samples for 10 minutes for serving as the control groups. The antioxidant activity and the total phenol contents are compared between the two groups.

Please refer to FIG. 1, which is a diagram showing the effect of the FIR materials of the present invention on the total phenol contents of tea. The spectrophotometric procedure of Gutfinger and the Folin-Ciocalteau reagent are used to measure the total phenol contents of the experimental and control groups. As shown, the result reveals a significant increase in the total phenol content of the three experimental groups, the distilled de-ionized water, the reverse osmosis water and the tap water, up to 10.5%, 12.41% and 37.2% respectively (as shown in Table 1), wherein the FIR materials have the biggest effect on the tap water.

TABLE 1

| | dd Water | | RO water | | Tap water | |
|---|---|---|---|---|---|---|
| | Experimental groups (A) | Control groups (B) | Experimental groups (A) | Control groups (B) | Experimental groups (A) | Control groups (B) |
| Average | 0.295 | 0.270 | 0.301 | 0.271 | 0.333 | 0.243 |
| Relativity $(A - B)/B \times 100(\%)$ | 10.5 | | 12.41 | | 37.20 | |
| P Value $(n = 5, \alpha = 0.05)$ | 0.003 | | 0.022 | | 0.0006 | |

Figure 2:
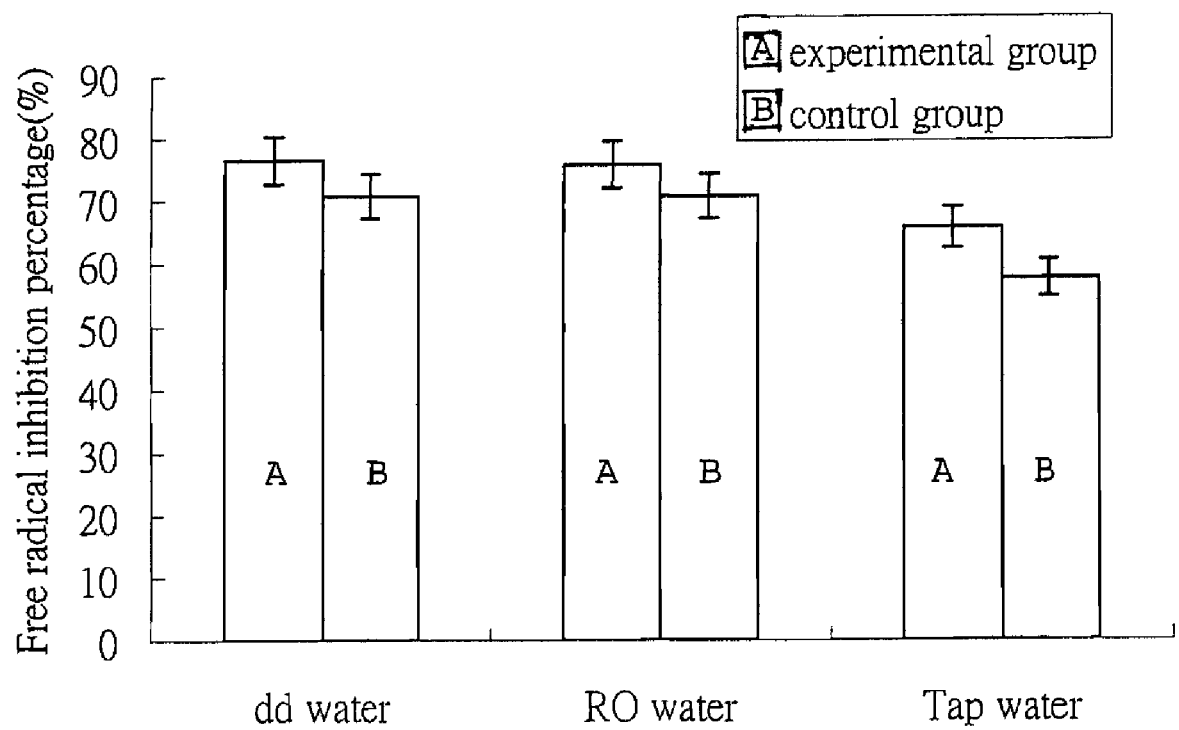
FIG. 2 is a diagram showing the effect of the FIR materials of the present invention on the antioxidant activity of tea.

Please refer to FIG. 2, which is a diagram showing the effect of the FIR materials of the present invention on the antioxidant activity of tea. The antioxidant activity of the tea is evaluated by the method of N, N-dimethyl-pphenylenediamine (DMPD) assay. In the DMPD assay, a defined amount of free radicals is provided, and the sample with a better antioxidant ability will scavenge more free radicals and has a higher inhibition percentage of the free radicals. As shown, the treatments of the FIR materials have effects of increasing the antioxidant ability from 7.1 to 13.99% on all the three experimental groups, wherein the FIR materials have the biggest effect on the tap water (as shown in Table 2).

TABLE 2

| | dd Water | | RO water | | Tap water | |
|---|---|---|---|---|---|---|
| | Experimental groups (A) | Control groups (B) | Experimental groups (A) | Control groups (B) | Experimental groups (A) | Control groups (B) |
| Average | 76.60 | 70.79 | 75.75 | 70.73 | 65.62 | 57.56 |
| Relativity $(A - B)/B \times 100(\%)$ | 8.21 | | 7.10 | | 13.99 | |
| P Value $(n = 5, \alpha = 0.05)$ | 0.0027 | | 0.0120 | | 0.0026 | |

According to the above two tables, it is apparent that the FIR materials have a significant effect on the tap water. The FIR materials increase the phenol content, such as catechins, in the liquid of the experimental groups by affecting water molecules under room temperature, which results in increasing the antioxidant constituents and ability of the tea. The treatments by the FIR materials in this embodiment are performed under room temperature and then the pretreated water is used to produce "Cold-making tea". However, if the pretreated water is boiled before making the tea, the effects in this embodiment still could be achieved.

The first embodiment is carried out by the decoction method; the second embodiment is carried out by the organic solvent extraction method; and the third embodiment is carried out by the immersion method, wherein all the three embodiments are achieved by the solvent extraction method, which dissolves the target effective constituents from plants according to the different solubility of various compositions in plants, and the solvent in which the target effective constituents have a higher solubility will be chosen. The methods for extracting the effective constituents still include the vapor-distillation method, which is suitable for the extraction of the effective constituents that will not be damaged by the vapor, such as some alkaloids with small molecules. The water in the vapor-distillation method also could be treated with the FIR materials before boiling. Regarding other methods for extracting the effective constituents and even the further processes of the separation and the purification, as long as the process relates to dissolving the effective constituents in a solvent, the solvent could be pretreated with the FIR materials of the present invention for achieving the purpose of increasing an amount of effective constituents from a plant in a solvent.

The composition of the FIR materials used in the present invention comes from natural minerals, and it is confirmed by specific machines that the FIR materials are able to generate negative ions without any detectable ionizing radiation. So far, the ionizing radiation is still considered a possible carcinogen capable of causing all known types of genetic mutations. In order to increase the FIR emissivity, many existing FIR products contain too many rare elements, which cause the users to expose to high level of ionizing radiation from the FIR products without any realization. The FIR materials of the present invention have high level of FIR emissivity without the consideration of the hazardous ionizing radiation, and therefore, the product produced by the present invention is healthy and safe.

While the invention has been described in terms of what is presently considered to be the most practical and preferred embodiments, it is to be understood that the invention needs not be limited to the disclose embodiments. Therefore, it is intended to cover various modifications and similar arrangements included within the spirit and scope of the appended claims, which are to be accorded with the broadest interpretation so as to encompass all such modifications and similar structures.

What is claimed is:

1. A method for increasing an amount of effective constituents from a plant within an extract solvent thereof comprising the steps of:
    treating an extraction solvent with a far-infrared (FIR) radiating material comprising 60-95% by weight of an aluminum oxide; and
    extracting effective constituents from the plant with the treated extraction solvent for a suitable time so as to obtain an extract containing an increased amount of the effective constituents dissolved therein.

2. The method as claimed in claim 1, further comprising a step of cooling the extract after the step of extracting the effective constituents from the plant.

3. The method as claimed in claim 1, further comprising a step of heating the treated solvent before the step of extracting the effective constituents from the plant.

4. The method as claimed in claim 1, wherein the step of treating the solvent with the FIR radiating material is performed under room temperature by placing the FIR radiating material to be near the solvent.

5. The method as claimed in claim 1, wherein the FIR radiating material comprises 1-20% by weight of an iron oxide.

6. The method as claimed in claim 1, wherein the FIR radiating material comprises 1-20% by weight of a magnesium oxide.

7. The method as claimed in claim 1, wherein the FIR radiating material comprises 1-30% by weight of a calcium carbonate.

8. The method as claimed in claim 1, wherein the solvent is a liquid.

9. The method as claimed in claim 1, wherein the solvent is one of a water and an organic solvent.

10. The method as claimed in claim 1, wherein the plant is a Chinese herb and the effective constituents are chemical constituents.

* * * * *